United States Patent
Ren et al.

(10) Patent No.: US 12,391,696 B2
(45) Date of Patent: Aug. 19, 2025

(54) PYRROLOPYRAZOLE DERIVATIVES, PREPARATION METHOD THEREOF AND APPLICATION THEREOF IN MEDICINE

(71) Applicants: SHANGHAI MEDICILON INC., Shanghai (CN); MEDICILON PRECLINICAL RESEARCH (SHANGHAI) LLC., Shanghai (CN)

(72) Inventors: Feng Ren, Shanghai (CN); Xianlian Wang, Shanghai (CN); Yongmei Xu, Shanghai (CN); Chunlin Chen, Shanghai (CN); Jinna Cai, Shanghai (CN)

(73) Assignees: SHANGHAI MEDICILON INC., Shanghai (CN); MEDICILON PRECLINICAL RESEARCH (SHANGHAI) LLC., Shanghai (CN)

( * ) Notice: Subject to any disclaimer, the term of this patent is extended or adjusted under 35 U.S.C. 154(b) by 879 days.

(21) Appl. No.: 17/630,110

(22) PCT Filed: Aug. 26, 2019

(86) PCT No.: PCT/CN2019/102525
§ 371 (c)(1),
(2) Date: Jan. 25, 2022

(87) PCT Pub. No.: WO2021/017067
PCT Pub. Date: Feb. 4, 2021

(65) Prior Publication Data
US 2022/0281877 A1    Sep. 8, 2022

(30) Foreign Application Priority Data

Jul. 26, 2019   (CN) .......................... 201910683538.X

(51) Int. Cl.
*C07D 487/04*   (2006.01)
*A61P 1/04*   (2006.01)

(52) U.S. Cl.
CPC .............. *C07D 487/04* (2013.01); *A61P 1/04* (2018.01)

(58) Field of Classification Search
CPC ................................. C07D 487/04; A61P 1/04
See application file for complete search history.

(56) References Cited

FOREIGN PATENT DOCUMENTS

WO    WO-2019154366 A1 *  8/2019  ................ A61P 1/00

OTHER PUBLICATIONS

Google Patents Machine Translation of WO2019154366 in English (Year: 2019).*

* cited by examiner

*Primary Examiner* — Kortney L. Klinkel
*Assistant Examiner* — Richard Grant Peckham
(74) *Attorney, Agent, or Firm* — Alleman Hall & Tuttle LLP

(57) ABSTRACT

A novel type of pyrrolopyrazole derivatives shown in general formula (I), a preparation method thereof and application thereof or a pharmaceutical composition containing same as a therapeutic agent, particularly as a gastric acid secretion inhibitor and a potassium-competitive acid blocker (P-CABs) in biomedicine.

2 Claims, No Drawings

PYRROLOPYRAZOLE DERIVATIVES, PREPARATION METHOD THEREOF AND APPLICATION THEREOF IN MEDICINE

TECHNICAL FIELD

The present invention relates to a novel class of pyrrolopyrazole derivatives, to a process for their preparation, and to their use as therapeutic agents, especially as inhibitors of gastric acid secretion and as competitive acid blockers (P-CABs) of potassium ion, or pharmaceutical composition containing them.

BACKGROUND

Peptic ulcer mainly refers to chronic ulcer that occurs in stomach and duodenum. Although there are regional differences, the incidence of peptic ulcer usually accounts for 10% to 20% of the total population, and is a frequently-occurring disease or a common disease. Ulcer formation is due to various factors, and the digestion of the mucosa by acidic gastric juice is the essential factor in ulcer formation. Therefore, inhibition of gastric acid secretion is becoming the first method for the treatment of peptic ulcer diseases.

Since the first Proton Pump Inhibitors (PPIs) omeprazole was marketed in 1988, several products of PPIs have been marketed globally to date, including lansoprazole, pantoprazole, rabeprazole, and esomeprazole. PPIs have become the first choice drugs for the treatment of gastric acid-related diseases, including peptic ulcer, reflux esophagitis and Zollinger-Ehrlich syndrome. The Proton Pump is essentially $H^+/K^+$-adenosine triphosphatase ($H^+/K^+$-ATPase), which specifically pumps protons ($H^+$) into the stomach cavity to form a strong acid in the stomach. Proton Pump inhibitors can inhibit the activity of the proton pump and thereby regulate the secretion of gastric acid mediated by the proton pump.

Potassium-Competitive Acid Blockers (P-CABs) are a novel class of gastric acid blockers thus play a role in inhibiting the enzyme activity of H+/K+-ATPase by reversibly binding $H^+/K^+$-ATPase competitively with potassium ions ($K^+$). Compared with PPIs, the P-CABs have the characteristics of lipophilicity, alkalescence, stability under acidic (low pH) conditions and the like. At the same time, the P-CABs have the advantages of quick response, easier achievement of acid inhibition effect and the like.

The first new P-CABs drug Voronolazan was marketed in Japan in 2014 for the treatment of gastric acid-related diseases such as peptic ulcer. A series of the structures of potassium ion-competitive acid blockers have also been disclosed. However, there is still a need to develop new compounds with diversified structural types and better medicinal properties.

SUMMARY

In view of the above-mentioned problems, the object of the present invention is to provide a compound for treating gastric acid-related diseases such as peptic ulcer, which is of a novel structural type and has excellent effects and actions.

In a first aspect, the present invention provides a compound represented by general formula (I) or a pharmaceutically acceptable salt thereof,

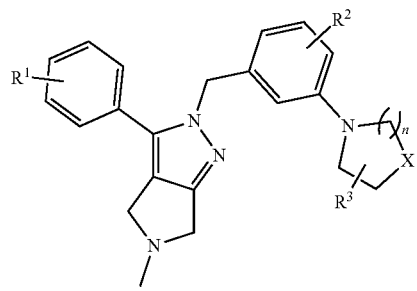

Wherein:
$R^1$ is selected from hydrogen atom, halogen or alkyl;
$R^2$ is selected from hydrogen atom, halogen, hydroxyl or alkyl;
n=1 or 2;
$R^3$ is connected to carbon atom or X;
when $R^3$ is connected to carbon atom and X is selected from $CH_2$, O or $NR^a$, wherein $R^a$ is selected from hydrogen atom or alkyl, and $R^3$ is selected from hydrogen atom, hydroxyl group, alkyl or $NR^bR^c$, wherein $R^b$ and $R^c$ are each independently selected from $C_{1-3}$ alkyl, or $R^b$ and $R^c$ are linked together and form a four-membered, five-membered, six-membered or seven-membered heterocyclic ring with the N to which they are linked;
when $R^3$ is connected to X, and X is selected from CH, O Or N, $R^3$ does not exist or is selected from hydrogen atom, alkyl or $NR^bR^c$, wherein $R^b$ and $R^c$ are each independently selected from $C_{1-3}$ alkyl groups, or $R^b$ and $R^c$ are linked together and form a four-membered, five-membered, six-membered or seven-membered heterocyclic ring with the N to which they are linked.
Preferably, $R^1$ is fluorine atom;
$R^2$ is hydrogen atom;
n=1 or 2;
$R^3$ is connected to X, X is selected from CH, O or N, $R^3$ does not exist or is selected from hydrogen atom, methyl, and piperidinyl.
Preferably, the compound is selected from:
4-(3-((3-(2-fluorophenyl)-5-methyl-5,6-dihydropyrrolo[3,4-c]pyrazole-2(4H)-yl)methyl) phenyl)morpholine;
3-(2-fluorophenyl)-5-methyl-2-(3-(piperidin-1-yl)benzyl)-2,4,5,6-tetrahydropyrrolo[3,4-c] pyrazole;
3-(2-fluorophenyl)-5-methyl-2-(3-(pyrrolidin-1-yl)benzyl)-2,4,5,6-tetrahydropyrrolo[3,4-c] pyrazole;
3-(2-fluorophenyl)-5-methyl-2-(3-(4-methylpiperazin-1-yl) benzyl)-2,4,5,6-tetrahydropyrrolo[3,4-c]pyrazole;
2-(3-([1,4'-bipiperidine]-1'-yl)benzyl)-3-(2-fluorophenyl)-5-methyl-2,4,5,6-tetrahydropyrrolo[3,4-c]pyrazole.

In a second aspect, the present invention provides a pharmaceutical composition, comprising the compound represented by general formula (I) or a pharmaceutically acceptable salt thereof and a pharmaceutically acceptable carrier, excipient or diluent.

In a third aspect, the present invention provides an application of the compound represented by general formula (I) or the pharmaceutically acceptable salt thereof, and the above-mentioned pharmaceutical composition in preparing a gastric acid secretion inhibitor.

In a fourth aspect, the present invention provides an application of the compound represented by general formula (I) or the pharmaceutically acceptable salt thereof, and the above-mentioned pharmaceutical composition in preparing an H+/K+-adenosine triphosphatase inhibitor.

In a fifth aspect, the present invention provides an application of the compound represented by general formula (I) or the pharmaceutically acceptable salt thereof, and the above-mentioned pharmaceutical composition in preparing a potassium ion competitive acid blocker.

In a sixth aspect, the present invention provides an application of the compound represented by general formula (I) or the pharmaceutically acceptable salt thereof, and the above-mentioned pharmaceutical composition in preparing a medicament for the treatment and/or prevention of peptic ulcer, Zollinger-Ellison Syndrome, gastritis, erosive esophagitis, reflux esophagitis, symptomatic gastroesophageal reflux disease, Barrett's esophagitis, functional dyspepsia, *Helicobacter pylori* infection, gastric cancer, gastric MALT lymphoma, ulcers caused by non-steroidal anti-inflammatory drugs, or hyperacidity or ulcers caused by post-operative stress; or inhibiting peptic ulcer, acute stress ulcer, hemorrhagic gastritis, or upper gastrointestinal bleeding caused by invasive stress.

DETAILED DESCRIPTION

The present invention will be further described below through the following embodiments. It should be understood that the following embodiments are only used to illustrate the present invention, not to limit the present invention.

Unless stated to the contrary, the following terms used in the specification and claims have the following meanings.

The term "alkyl" refers to a saturated aliphatic hydrocarbon group, including straight or branched chain groups of 1 to 10 carbon atoms. Preferably, an alkyl groups containing 1 to 5 carbon atoms. More preferably, an alkyl group containing 1 to 3 carbon atoms, such as methyl, ethyl, n-propyl, isopropyl.

The carbon atom content of various hydrocarbon containing moieties is indicated by the prefix designating the minimum and maximum number of carbon atoms for that moiety, i.e., the prefixes indicate that the number of carbon atoms for that moiety ranges from integers "i" to integers "j" (including i and j). Thus, for example, $C_{1-3}$ alkyl refers to alkyl groups of 1 to 3 carbon atoms (including 1 and 3).

The term "hydroxy" refers to an —OH group.

The term "halogen" refers to fluorine, chlorine, bromine or iodine.

The term "heterocyclic ring" refers to a ring having at least one saturated or unsaturated ring. In addition to carbon atoms, the atoms constituting the ring also comprise at least one hetero atom, such as nitrogen, oxygen, and sulfur atoms, preferably at least one nitrogen atom. Examples of heterocycles include non-aromatic heterocycles (or aliphatic heterocycles), such as morpholine, piperidine, pyrrolidine; and heteroaromatic rings (or aromatic heterocycles), such as furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxazole, carbazole and quinazoline.

Unless otherwise specified, all occurrences of the compounds herein are intended to comprise all possible isomers, such as tautomers, enantiomers, diastereomers, and mixtures thereof.

The term "compound of the present invention" refers to a compound represented by the general formula (I). The term also comprises various crystalline forms of the compound of general formula (I), pharmaceutically acceptable salts, hydrates or solvates.

The term "pharmaceutically acceptable salt" refers to salts formed by the compounds of the present invention with acids or bases that are suitable for use as pharmaceutical agents. Pharmaceutically acceptable salts include inorganic salts and organic salts. One preferred class of salts is that formed from the compounds of the present invention and acids. Suitable acids for forming salt include, but are not limited to: inorganic acids such as hydrochloric acid, hydrobromic acid, hydrofluoric acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid, benzenesulfonic acid, etc.; and acidic amino acids such as aspartic acid and glutamic acid.

The term "pharmaceutically acceptable carrier" refers to a carrier that can be used in the preparation of pharmaceutical compositions, which are generally safe, non-toxic, not biologically or otherwise undesirable, and comprises carriers that are pharmaceutically acceptable by animals and humans. As used in the specification and claims, a "pharmaceutically acceptable carrier" comprises one or more such carriers.

The terms "comprise", "contain" or "include" mean that various ingredients may be used together in a mixture or composition of the present invention. Therefore, the terms "mainly consist of" and "consist of" are encompassed by the term "comprise".

The term "prevention" refers, for example, to the prevention of development of clinical symptoms of a disease in a mammal that may be exposed to or predisposed to the disease but has not yet experienced or displayed symptoms of the disease.

The term "treatment" may refer to inhibiting a disease, such as preventing or reducing the development of a disease or clinical symptoms thereof, or relieving a disease, such as causing regression of a disease or clinical symptoms thereof.

Compound of General Formula (I)

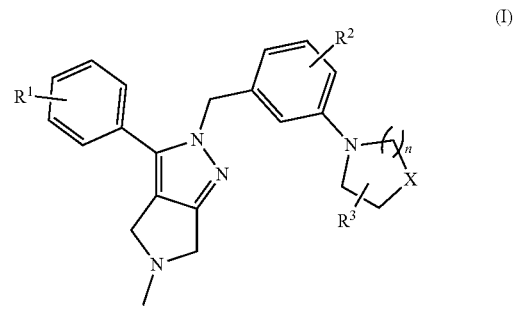

(I)

In some embodiments of the present invention, $R^1$ is selected from hydrogen atom, halogen or alkyl. In a more preferred embodiment, $R^1$ is fluorine atom. The substitution site for $R^1$ is preferably at the 2 position.

In some embodiments of the present invention, $R^2$ is selected from hydrogen atom, halogen, hydroxyl, or alkyl. In a more preferred embodiment, $R^2$ is hydrogen atom.

In some embodiments of the present invention, n=1 or 2.

In some embodiments of the present invention, $R^3$ is connected to carbon atom other than X. In this case, $R^3$ can be selected from hydrogen atom, hydroxyl group, alkyl or NR$^b$R$^c$, wherein R$^b$ and R$^c$ are selected from C$_{1-3}$ alkyl, or R$^b$ and R$^c$ are linked together and form a four-membered, five-membered, six-membered or seven-membered heterocyclic ring with the N to which they are linked. X can be selected from CH$_2$, O or NR$^a$, wherein R$^a$ is selected from hydrogen atom or alkyl.

In some embodiments of the present invention, R$^3$ is connected to X. In this case, X can be selected from CH, O, or N. R$^3$ may be absent or is selected from hydrogen atom, hydroxyl group, alkyl or NR$^b$R$^c$, wherein R$^b$ and R$^c$ are selected from C$_{1-3}$ alkyl groups, R$^b$ and R$^c$ are linked together and form a four-membered, five-membered, six-membered or seven-membered heterocyclic ring with the N to which they are linked. X can be selected from CH$_2$, O or NR$^a$, wherein R$^a$ is selected from hydrogen atom or alkyl.

In a preferred embodiment, R$^3$ is connected to X, X is selected from CH, O, N or R$^3$ is absent or is selected from hydrogen atom, methyl, and piperidinyl.

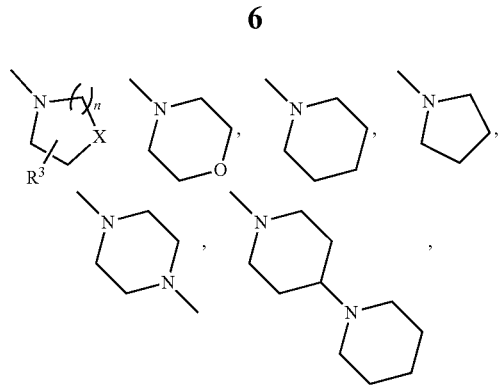

In some embodiments of the present invention, the compound of general formula (I) is selected from the compounds shown in Table 1

TABLE 1

| Compound number | Compound structure | Compound naming |
|---|---|---|
| 1 | 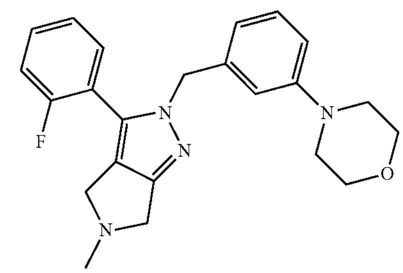 [SMILES: CN1Cc2nn(Cc3cccc(N4CCOCC4)c3)c(-c3ccccc3F)c2C1] | 4-(3-((3-(2-fluorophenyl)-5-methyl-5,6-dihydropyrrolo[3,4-c]pyrazole-2(4H)-yl)methyl)phenyl)morpholine |
| 2 | 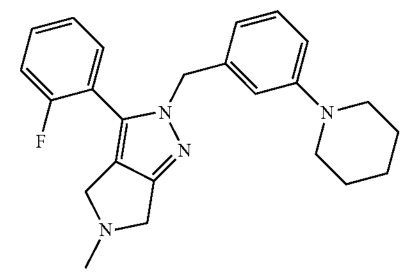 [SMILES: CN1Cc2nn(Cc3cccc(N4CCCCC4)c3)c(-c3ccccc3F)c2C1] | 3-(2-fluorophenyl)-5-methyl-2-(3-(piperidin-1-yl)benzyl)-2,4,5,6-tetrahydropyrrolo[3,4-c]pyrazole |
| 3 | 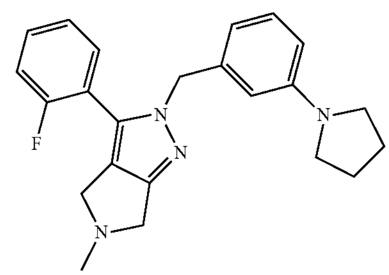 [SMILES: CN1Cc2nn(Cc3cccc(N4CCCC4)c3)c(-c3ccccc3F)c2C1] | 3-(2-fluorophenyl)-5-methyl-2-(3-(pyrrolidin-1-yl)benzyl)-2,4,5,6-tetrahydropyrrolo[3,4-c]pyrazole |
| 4 | 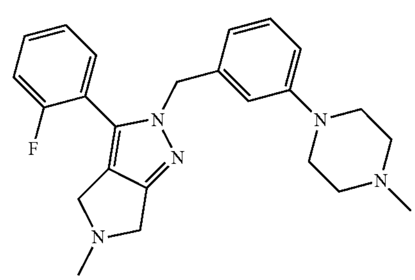 [SMILES: CN1CCN(c2cccc(Cn3nc4c(c3-c3ccccc3F)CN(C)C4)c2)CC1] | (2-fluorophenyl)-5-methyl-2-(3-(4-methylpiperazin-1-yl)benzyl)-2,4,5,6-tetrahydropyrrolo[3,4-c]pyrazole |

TABLE 1-continued

| Compound number | Compound structure | Compound naming |
| --- | --- | --- |
| 5 | 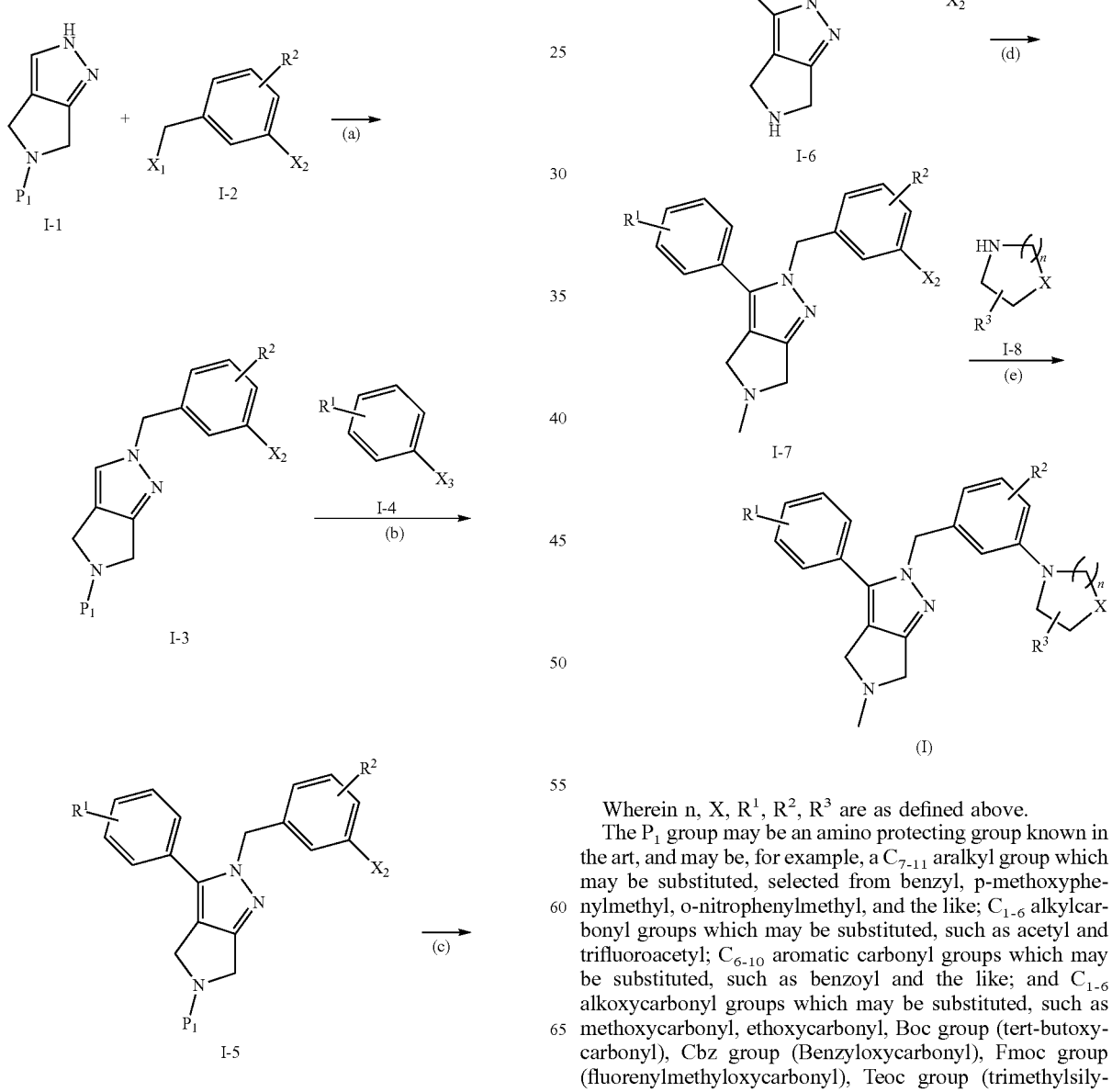 | (3-([1,4'-bipiperidine]-1'-yl)benzyl)-3-(2-fluorophenyl)-5-methyl-2,4,5,6-tetrahydropyrrolo[3,4-c]pyrazole |

Preparation Method of Compound of General Formula (I)

In some embodiments of the present invention, the compound of general formula (I) may be prepared using the following general synthetic route 1:

Wherein n, X, $R^1$, $R^2$, $R^3$ are as defined above.

The $P_1$ group may be an amino protecting group known in the art, and may be, for example, a $C_{7-11}$ aralkyl group which may be substituted, selected from benzyl, p-methoxyphenylmethyl, o-nitrophenylmethyl, and the like; $C_{1-6}$ alkylcarbonyl groups which may be substituted, such as acetyl and trifluoroacetyl; $C_{6-10}$ aromatic carbonyl groups which may be substituted, such as benzoyl and the like; and $C_{1-6}$ alkoxycarbonyl groups which may be substituted, such as methoxycarbonyl, ethoxycarbonyl, Boc group (tert-butoxycarbonyl), Cbz group (Benzyloxycarbonyl), Fmoc group (fluorenylmethyloxycarbonyl), Teoc group (trimethylsilylethoxycarbonyl) and the like; alkenyloxycarbonyl groups such as Alloc group (allyloxycarbonyl) and the like; alkylsulfonyl groups such as methylsulfonyl and the like; $C_{6-10}$ arylsulfonyl groups which may be substituted, such as p-toluenesulfonyl and the like.

The $X_1$ group may be a leaving group known in the art, and may be selected from, for example, halogen atom such as fluorine atom, chlorine atom, bromine atom, iodine atom, etc.

The $X_2$ group may be selected from halogen atom such as chlorine atom, bromine atom, iodine atom, etc.

The $X_3$ group can be selected from halogen atom such as chlorine atom, bromine atom, iodine atom, etc.

In step (a), the compound of formula I-1 is reacted with the compound of formula I-2 to obtain the compound of formula I-3.

The molar ratio of the compound of formula I-1 to the compound of formula I-2 can be 1: (0.5 to 3.0). The reaction solvent may be acetonitrile, acetone, tetrahydrofuran, dioxane, N,N-dimethylformamide, etc. The reaction of step (a) may be carried out in the presence of a base. The base can be selected from: cesium carbonate, potassium carbonate, sodium carbonate, potassium hydroxide, sodium hydroxide, and the like. The molar ratio of the compound of formula I-1 to the base can be 1: (1.0 to 6.0). The reaction temperature of step (a) may be appropriately set by those skilled in the art, and may be, for example, 0 to 100° C.

In step (b), the compound of formula I-3 is reacted with the compound of formula I-4 to obtain the compound of formula I-5.

The molar ratio of the compound of formula I-3 to the compound of formula I-4 can be 1: (0.5 to 3.0). The reaction solvent may be acetonitrile, acetone, tetrahydrofuran, dioxane, N,N-dimethylformamide, etc. Step (b) may be carried out in the presence of a palladium catalyst. The palladium catalyst can be selected from: allylpalladium(II) chloride dimer, tris(dibenzylideneacetone)dipalladium, [1,1'-bis(diphenylphosphino)ferrocene] Palladium dichloride, palladium chloride, and the like. Alternatively, the reaction of step (b) may be carried out in the presence of a base. The base may be selected from: potassium acetate, sodium acetate, potassium phosphate, potassium dihydrogen phosphate, potassium bistrimethylsilylamine, sodium bistrimethylsilylamine, and the like. The molar ratio of the compound of formula I-3 to the base can be 1: (0.5 to 3.0). The reaction temperature in step (b) may be appropriately set by those skilled in the art, and may be, for example, 40 to 150° C.

In step (c), the $P_1$ protecting group is removed. The reaction conditions may be those commonly used in the art for deprotecting an amino protecting group. For example, when P1 is Boc, it can be treated with a protic acid (for example, trifluoroacetic acid) or a Lewis acid.

In step (d), the compound of formula I-6 is subjected to an aminomethylation reaction to obtain the compound of formula I-7. This step may employ aminomethylation reaction conditions well known in the art. In some embodiments, the compound of formula I-6 is stirred with formaldehyde for a period of time to generate a Schiff base, and then reacted with a reducing agent such as sodium borohydride acetate, for a period of time to obtain the compound of formula I-7.

In step (e), the compound of formula I-7 is reacted with a compound of formula I-8 to obtain a compound of general formula (I).

The molar ratio of the compound of formula I-7 to the compound of formula I-8 can be 1: (0.5 to 5.0). The reaction solvent may be dioxane, tetrahydrofuran, toluene, N,N-dimethylformamide, and the like. Step (e) may be carried out in the presence of a palladium catalyst. The palladium catalyst may be selected from: tris(dibenzylideneacetone) dipalladium ($Pd_2(dba)_3$), allyl palladium(II) chloride dimer, [1,1'-bis(diphenyl) Phosphonyl) ferrocene] palladium dichloride, palladium chloride, and the like. In addition, in the reaction of step (e), phosphine ligands can also be added, such as 2-dicyclohexylphosphorus-2',4',6'-triisopropylbiphenyl d (X-phos), 4,5-bisdiphenylphosphine-9,9-dimethylxanthene (Xant-phos), 1,1'-binaphthalene-2,2'-bisdiphenylphosphine (BINAP), tricyclohexylphosphine, and the like. The reaction of step (e) may be carried out in the presence of a base. The base may be selected from: sodium tert-butoxide, cesium carbonate, sodium carbonate, sodium bicarbonate, potassium phosphate, and the like. The molar ratio of the compound of formula I-7 to the base can be 1: (0.5-5.0). The reaction temperature of step (e) can be appropriately set by those skilled in the art, and can be, for example, 40 to 150° C.

Application of the Compounds of General Formula (I)

The compounds of general formula (I) can be used as inhibitors of gastric acid secretion.

The compounds of general formula (I) can be used as $H^+/K^+$-ATPase inhibitors.

The compounds of general formula (I) can be used as potassium ion competitive acid blockers (P-CABs).

The compounds of general formula (I) can be used for treating and/or preventing peptic ulcer, Zollinger-Ehrlich syndrome, gastritis, erosive esophagitis, reflux esophagitis, symptomatic gastroesophageal reflux disease, Barrett's esophagitis, functional dyspepsia, *Helicobacter pylori* infection, gastric cancer, gastric MALT lymphoma, ulcers caused by non-steroidal anti-inflammatory drugs, or hyperacidity or ulcers caused by post-operative stress; or inhibiting peptic ulcers, acute stress ulcers, Haemorrhagic gastritis or upper gastrointestinal bleeding caused by invasive stress. The aforementioned peptic ulcer includes but is not limited to gastric ulcer, duodenal ulcer or anastomotic ulcer. Symptomatic gastroesophageal reflux disease includes but is not limited to non-erosive reflux disease or gastroesophageal reflux disease without esophagitis.

Pharmaceutical Composition

The pharmaceutical composition of the present invention comprises an effective amount of the compound represented by the general formula (I) or tautomer, enantiomer, diastereomer, and mixture form thereof, pharmaceutically acceptable salts thereof, and pharmaceutically acceptable carrier or excipient or diluent.

"Effective amount" means the compound of the present invention: (i) treating a particular disease, condition or disorder, (ii) attenuating, ameliorating or eliminating one or more symptoms of a particular disease, condition or disorder, or (iii) preventing or delaying the onset of one or more symptoms of a particular disease, condition, or disorder described herein.

Examples of pharmaceutically acceptable carriers moieties are cellulose and its derivatives (e.g., sodium carboxymethyl cellulose, sodium ethyl cellulose, cellulose acetate, etc), gelatin, talc, and solid lubricants (e.g., stearic acid, magnesium stearate), calcium sulfate, vegetable oils (e.g., soybean oil, sesame oil, peanut oil, olive oil, etc.), polyols (e.g., propylene glycol, glycerin, mannitol, sorbitol, etc), emulsifiers (e.g., Tween), wetting agents (e.g., sodium lauryl sulfate), colorants, flavors, stabilizers, antioxidants, preservatives, pyrogen-free water, and the like.

The mode of administration of the compounds or pharmaceutical compositions of the present invention is not particularly limited, and representative mode of administration include (but are not limited to): oral, intratumoral, rectal, parenteral (intravenous, intramuscular, or subcutaneous), and topical administration.

The compounds of the present invention may be administered alone or in combination with other pharmaceutically acceptable compounds.

Another aspect of the present invention relates to a method of inhibiting the secretion of gastric acid, which comprises administering to a patient in need of an effective amount of the compound represented by the general formula (I) or its tautomers, enantiomers, and diastereomers, and mixtures thereof, and pharmaceutically acceptable salts or pharmaceutical compositions thereof.

Another aspect of the present invention relates to a method for inhibiting $H^+/K^+$-adenosine triphosphatase ($H^+/K^+$-ATPase) comprising administering to a patient in need of an effective amount of the compound of formula (I) or its tautomers, enantiomers, diastereomers, and mixtures thereof, and pharmaceutically acceptable salts thereof or pharmaceutical compositions thereof.

Hereinafter, the present invention will be further described with the specific examples. It should be understood that the following examples are used to explain this invention and do not mean to limit the scope of this invention. The experimental methods that do not indicate specific conditions in the following examples usually follow the conventional conditions or the conditions recommended by the manufacturer. Unless otherwise stated, percentages and parts are calculated by weight.

The structure of the compound is determined by nuclear magnetic resonance (NMR) or mass spectrometry (MS), and the purity of the compound is determined by liquid high pressure chromatography (HPLC). NMR was measured using a Bruker AVANCE-400 nuclear magnetic resonance apparatus in deuterated dimethyl sulfoxide (DMSO-d6) or deuterated methanol (MeOH-d4) as the solvent and tetramethylsilane (TMS) as the internal standard and chemical shifts in ppm. MS was determined using Agilent 6120 mass spectrometer. HPLC was measured using an Agilent 1200DAD high pressure liquid chromatograph.

Example 1

4-(3-((3-(2-fluorophenyl)-5-methyl-5,6-dihydropyrrolo [3,4-c] pyrazole-2(4H)-yl) methyl) phenyl) morpholine

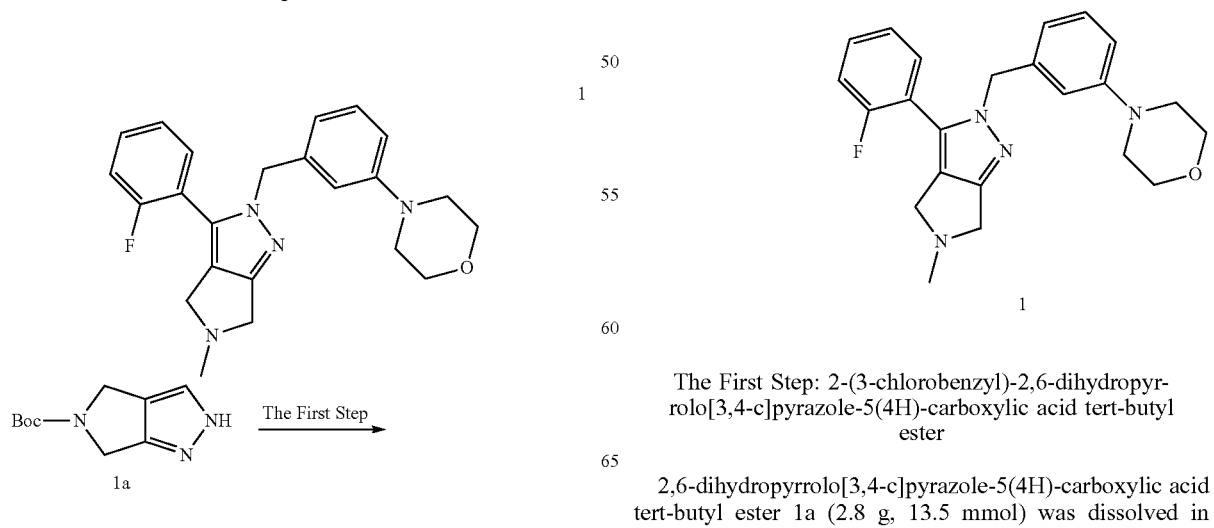

The First Step: 2-(3-chlorobenzyl)-2,6-dihydropyrrolo[3,4-c]pyrazole-5(4H)-carboxylic acid tert-butyl ester 2,6-dihydropyrrolo[3,4-c]pyrazole-5(4H)-carboxylic acid tert-butyl ester 1a (2.8 g, 13.5 mmol) was dissolved in acetonitrile (50 mL) and 3-chlorobenzyl Bromine (3.3 g, 16.2 mmol) and cesium carbonate (32.5 g, 47 mmol) were added, the mixture was purged with nitrogen for 3 times, and placed in an 80° C. oil bath at for reaction for 3 hours. The reaction solution was filtered, and the filtrate was concentrated. The residue was purified by column chromatography (petroleum ether: ethyl acetate=2:1) to obtain 2-(3-Chlorobenzyl)-2,6-dihydropyrrolo[3,4-c]pyrazole-5(4H)-carboxylic acid tert-butyl ester 1b (4.1 g, yellow oil), the yield was 91%. MS m/z (ESI): 334.1 [M+H].

The Second Step: 2-(3-chlorobenzyl)-3-(2-fluorophenyl)-2,6-dihydropyrrolo [3,4-c] pyrazole-5(4H)-carboxylic acid tert butyl 2-(3-chlorobenzyl)-2, 6-dihydropyrrolo[3,4-c]pyrazole-5 (4H)-carboxylic acid tert-butyl ester 1b (4.6 g, 13.7 mmol), potassium acetate (8 g, 82.2 mmol), allylpalladium(II) chloride dimer (499 mg, 1.37 mmol), N,N-dimethylacetamide (50 mL) and o-fluoroiodobenzene (6.1 g, 27.4 mmol) were added in a round bottom flask in turns. After the oil pump was purged (argon) for four times, the mixture was placed in an oil bath that was raised to 100° C. in advance for reaction for 3 hours. After the reaction returned to room temperature, the reaction solution was poured directly into water (80 mL), and extracted with ethyl acetate (40 mL×3). The organic phase was washed with brine (40 mL×2), then dried over anhydrous sodium sulfate, filtered and concentrated. The crude product was separated by column chromatography (petroleum ether/ethyl acetate=3/1) to obtain 2-(3-chlorobenzyl)-3-(2-fluorophenyl)-2,6-dihydropyrrolo[3, 4-c] pyrazole-5(4H)-tert-butyl carboxylate 1c (1.21 g, yellow oil), yield: 20.6%. MS m/z (ESI): 428.3 [M+H].

The Third Step: 2-(3-chlorobenzyl)-3-(2-fluorophenyl)-2,4,5,6-tetrahydropyrrolo[3,4-c] pyrazole Trifluoroacetic acid (0.5 mL) was added into 2-(3-chlorobenzyl)-3-(2-fluorophenyl)-2,6-dihydropyrrolo [3,4-c] pyrazole-5(4H)-Carboxylic acid tert-butyl ester 1c (729 mg, 1.45 mmol) in dichloromethane (1.5 mL) solution for reaction at room temperature for 1 hour. After the reaction, the mixture was directly concentrated to obtain the crude product 2-(3-chlorobenzyl)-3-(2-fluorophenyl)-2,4,5,6-tetrahydropyrrolo [3,4-c] pyrazole 1d (581 mg, brown oil), yield: 100%. MS m/z(ESI): 328[M+1].

The Fourth Step: 2-(3-chlorobenzyl)-3-(2-fluorophenyl)-5-methyl-2,4,5,6-tetrahydropyrrolo[3,4-c] pyrazole Aqueous formaldehyde solution (37%, 1.2 g, 14.5 mmol) was added into 2-(3-chlorobenzyl)-3-(2-fluorophenyl)-2,4, 5,6-tetrahydropyrrolo[3, 4-c] Pyrazole 1d (581 mg, 1.45 mmol) in dichloromethane/methanol (6 mL, 2/1) solution, and the mixture was stirred at room temperature for half an hour. Sodium acetate borohydride (1.8 g, 8.7 mmol) was slowly added into the reaction solution for reaction at room temperature overnight. After the reaction solution was concentrated, the mixture was dissolved and diluted with dichloromethane (10 mL), and then washed with ammonia/water (10 mL×2, 1/5) and saturated brine (10 mL) in sequence. The organic phase was dried with anhydrous sodium sulfate and concentrated. 50 mg of crude product was taken and prepared by high pressure liquid chromatography (acetonitrile/water (containing 0.05% trifluoroacetic acid)) to obtain 2-(3-chlorobenzyl)-3-(2-fluorophenyl)-5-methyl-2,4,5,6-tetrahydropyrrolo[3,4-c]pyrazole 1e (trifluoroacetate, salt coefficient=1.3, 20.1 mg, yellow oil), yield: 24.5%. MS m/z(ESI): 341[M+1]. $^1$H NMR (400 MHz, CDCl 3) δ 7.38 (dt, J=9.5, 3.7 Hz, 1H), 7.17 (d, J=16.1 Hz, 1H), 7.09 (dd, J=22.2, 12.7 Hz, 2H), 6.99-6.77 (m, 2H), 5.15 (s, 2H), 4.82 (d, J=15.1 Hz, 2H), 4.03 (dd, J=28.1, 12.0 Hz, 2H), 3.04 (s, 4H).

The Fifth Step: 4-(3-((3-(2-fluorophenyl)-5-methyl-5,6-dihydropyrrolo [3,4-c] pyrazole-2(4H)-yl) methyl) phenyl) morpholine The compound 2-(3-chlorobenzyl)-3-(2-fluorophenyl)-5-methyl-2,4,5,6-tetrahydropyrrolo[3,4-c]pyrazole 1e (50 mg, 0.15 mmol) was dissolved in 1,4-dioxane (3 mL) solution, Morpholine (26 mg, 0.29 mmol), tris(dibenzylideneacetone) dipalladium (14 mg, 0.015 mmol), 2-dicyclohexylphosphorus-2',4',6'-triisopropylbiphenyl (14 mg, 0.029 mmol), sodium tert-butoxide (42 mg, 0.44 mmol) were added in sequence, and the mixture was reacted overnight at 100° C. in an argon atmosphere. The reaction solution was cooled to room temperature, poured into water (10 mL), and extracted with ethyl acetate (30 mL×3). The organic phase was combined and washed with saturated brine (20 mL×2), dried over anhydrous sodium sulfate, filtered and concentrated. The residue was prepared by HPLC (acetonitrile/water (containing 0.05% NH 3) gradient washing) to obtain compound 4-(3-((3-(2-fluorophenyl)-5-methyl-5,6-dihydropyrrolo[3,4-c]pyrazole-2(4H)-yl)methyl) Phenyl)morpholine (16 mg, yellow oil), yield: 25.5%. MS m/z (ESI): 393.3 [M+1]. $^1$H NMR (400 MHz, CDCl 3) δ 7.33-7.27 (m, 1H), 7.15 (m, 1H), 7.10-7.04 (m, 3H), 6.68 (dd, 1H), 6.49 (s, 1H), 6.43 (d, 1H), 5.12 (s, 2H), 3.77 (s, 2H), 3.74 (t, 4H), 3.66 (s, 2H), 2.98 (t, 4H), 2.56 (s, 3H).

Example 2

3-(2-fluorophenyl)-5-methyl-2-(3-(piperidin-1-yl) benzyl)-2,4,5,6-tetrahydropyrrolo[3,4-c]pyrazole

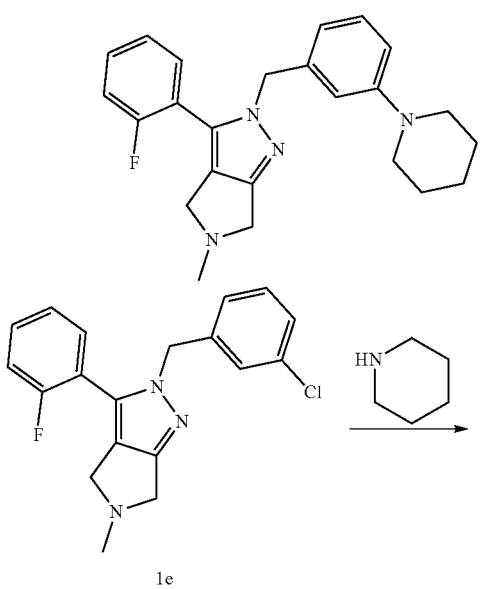

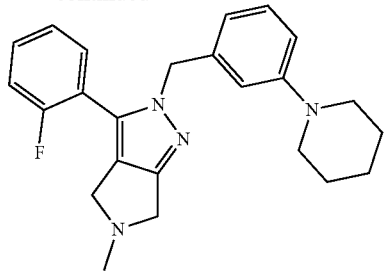

2

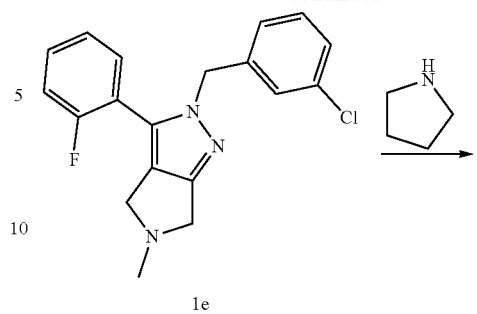

1e

The compound, 2-(3-chlorobenzyl)-3-(2-fluorophenyl)-5-methyl-2,4,5,6-tetrahydropyrrolo[3,4-c]pyrazole 1e (100 mg, 0.29 mmol) was dissolved in N,N-dimethylformamide (3 mL) solution, and piperidine (74 mg, 0.87 mmol), tris(dibenzylideneacetone) dipalladium (27 mg, 0.029 mmol), 2-Dicyclohexylphosphorus-2',4',6'-triisopropylbiphenyl (28 mg, 0.058 mmol) and cesium carbonate (189 mg, 0.58 mmol) were reacted at 110° C. overnight in an argon atmosphere. The reaction solution was cooled to room temperature, poured into water (10 mL), and extracted with ethyl acetate (20 mL×3). The organic phases were combined and washed with saturated brine (15 mL×2), dried over anhydrous sodium sulfate, filtered and concentrated. The residue was prepared by high HPLC (acetonitrile/water (containing 0.05% trifluoroacetic acid) gradient washing) to obtain the compound 3-(2-fluorophenyl)-5-methyl-2-(3-(piperidin-1-yl))benzyl)-2,4,5,6-tetrahydropyrrolo[3,4-c]pyrazole 2 (trifluoroacetate, salt coefficient=3.70, salt molecular weight: 812.39, 13 mg, light red oil Material), yield: 11.5%. MS m/z (ESI): 391.2 [M+1]. $^1$H NMR (400 MHz, CDCl 3) δ 7.47-7.34 (m, 3H), 7.30 (s, 1H), 7.26-7.21 (m, 2H), 7.19-7.15 (m, 2H), 5.30 (d, 2H), 4.91 (s, 2H), 4.27-4.12 (d, 2H), 3.43 (s, 4H), 3.17 (s, 3H), 2.07 (t, 4H), 1.73 (s, 2H).

Example 3

3-(2-fluorophenyl)-5-methyl-2-(3-(pyrrolidin-1-yl)benzyl)-2,4,5,6-tetrahydropyrrolo[3,4-c]pyrazole

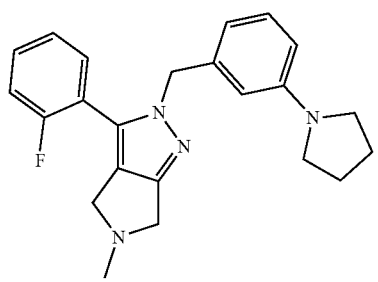

3

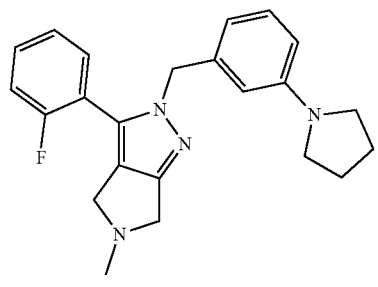

3

2-(3-Chlorobenzyl)-3-(2-fluorophenyl)-5-methyl-2,4,5,6-tetrahydropyrrolo[3,4-c]pyrazole 1e (0.15 g, 0.44 mmol), sodium tert-butoxide (0.12 g, 1.3 mmol), Pd$_2$(dba)$_3$ (40 mg, 0.044 mmol), 1,4-dioxane (5 mL), X-phos (41 mg, 0.088 mmol), pyrrolidine (0.62 g, 0.88 mmol) were added into a round bottom flask. After the oil pump was purged (argon) for four times, the mixture was placed in an oil bath that was raised to 100° C. in advance for reaction for 16 hours. After the reaction returned to room temperature, the reaction solution was poured directly into water (40 mL), and extracted with ethyl acetate (20 mL×3). The organic phase was washed with brine (20 mL×2), then dried over anhydrous sodium sulfate, filtered, and concentrated. The organic layer was concentrated and prepared by high pressure liquid chromatography (acetonitrile/water (containing 0.05% trifluoroacetic acid)) to obtain 3-(2-fluorophenyl)-5-methyl-2-(3-(pyrrolidin-1-yl)benzyl)-2,4,5,6-tetrahydropyrrolo[3,4-c]pyrazole 3 (trifluoroacetate, salt coefficient=2.4, 26.0 mg, yellow-brown oil), Rate: 3.5%. MS m/z (ESI): 377.2 [M+1]. $^1$H NMR (400 MHz, CDCl3) δ 7.38 (dt, J=7.3, 3.7 Hz, 1H), 7.22-7.06 (m, 4H), 6.77 (d, J=7.1 Hz, 1H), 6.59 (d, J=7.5 Hz, 1H), 6.54 (s, 1H), 5.19 (s, 2H), 4.84 (d, J=13.5 Hz, 2H)), 4.04 (dd, J=31.6, 12.2 Hz, 2H), 3.32 (s, 4H), 3.06 (s, 3H), 2.02 (t, J=6.4 Hz, 4H).

Example 4

3-(2-fluorophenyl)-5-methyl-2-(3-(4-methylpiperazin-1-yl) benzyl)-2,4,5,6-tetrahydro pyrrolo [3,4-c] pyrazole

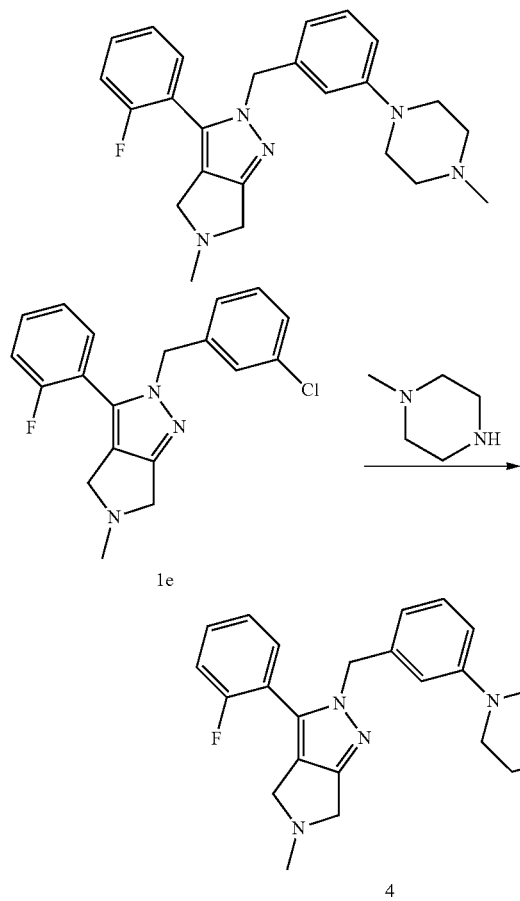

2-(3-chlorobenzyl)-3-(2-fluorophenyl)-5-methyl-2,4,5,6-tetrahydropyrrolo[3,4-c] pyrazole 1e (150 mg, 0.44 mmol), sodium tert-butoxide (0.13 g, 1.32 mmol), Pd 2(dba) 3 (40 mg, 0.044 mmol), X-phos (41 mg, 0.088 mmol), 1,4-Dioxane (5 mL), N-methylpiperazine (0.88 g, 0.88 mmol) were added into a round bottom flask. After the oil pump was purged (argon) for four times, the mixture was placed in an oil bath that was raised to 100° C. in advance for reaction for 16 hours. After the reaction returned to room temperature, the reaction solution was poured directly into water (40 mL), and extracted with ethyl acetate (20 mL×3). The organic phase was washed with brine (20 mL×2), then dried over anhydrous sodium sulfate, filtered, and concentrated. The organic layer was concentrated and prepared by high pressure liquid chromatography (acetonitrile/water (containing 0.05% trifluoroacetic acid)) to obtain 3-(2-fluorophenyl)-5-methyl-2-(3-(4-methylpiperidine) (Azin-1-yl)benzyl)-2,4,5,6-tetrahydro pyrrolo [3,4-c] pyrazole 4 (trifluoroacetate, salt coefficient=3.1, 79.9 mg, black oil), yield: 23.9%. MS m/z (ESI): 406.5 [M+1]. ¹H NMR (400 MHz, CDCl3) δ 7.37 (d, J=5.8 Hz, 1H), 7.20-7.01 (m, 4H), 6.72 (d, J=8.0 Hz, 1H), 6.53 (d, J=7.3 Hz, 1H), 6.42 (s, 1H), 5.15 (s, 2H), 4.80 (s, 2H), 4.01 (s, 2H), 3.49 (dd, J=23.9, 11.5 Hz, 4H), 3.07 (d, J=13.5 Hz, 2H), 3.04 (d, J=13.5 Hz, 3H), 2.94 (d, J=10.5 Hz, 2H), 2.76 (s, 3H).

Example 5

2-(3-([1,4'-Bipiperidine]-1'-yl)benzyl)-3-(2-fluorophenyl)-5-methyl-2,4,5,6-tetrahydropyrrolo[3,4-c] pyrazole

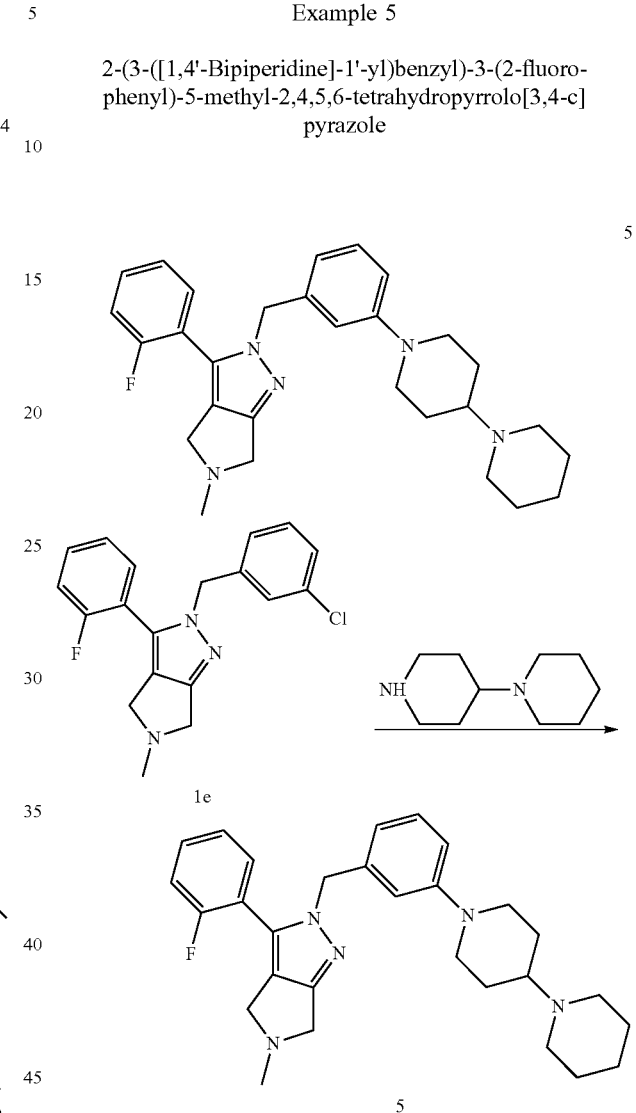

The compound 2-(3-chlorobenzyl)-3-(2-fluorophenyl)-5-methyl-2,4,5,6-tetrahydropyrrolo[3,4-c] pyrazole 1e (100 mg, 0.29 mmol) was dissolved in N,N-dimethylformamide (3 mL) solution, and 4-piperidinylpiperidine (168 mg, 0.87 mmol), tris(dibenzylideneacetone)dipalladium (27 mg, 0.029 mmol), 2-Dicyclohexylphosphorus-2',4',6'-triisopropylbiphenyl (28 mg, 0.058 mmol), cesium carbonate (189 mg, 0.58 mmol) were added in turns, the mixture was purged in an argon atmosphere at 110° C. for reaction overnight. The reaction solution was cooled to room temperature, poured into water (10 mL), and extracted with ethyl acetate (20 mL×3). The organic phases were combined and washed with saturated brine (15 mL×2), dried over anhydrous sodium sulfate, filtered and concentrated. The residue was prepared by HPLC (acetonitrile/water (containing 0.05% trifluoroacetic acid) gradient washing) to obtain compound 2-(3-([1,4'-bipiperidine]-1'-yl)benzyl)-3-(2-fluorophenyl)-5-methyl-2,4,5,6-tetra hydropyrrolo[3,4-c]pyrazole 5 (trifluoroacetate salt, 17 mg, brown solid), yield: 12.4%. MS m/z (ESI): 474.4 [M+1]. $^1$H NMR (400 MHz, MeOD) δ 7.52 (m, 1H), 7.39 (m, 1H), 7.27 (m, 2H), 7.12 (t, 1H), 6.90 (m, 1H), 6.65 (s, 1H), 6.51 (d, 1H), 5.29 (s, 2H), 3.70 (d, 2H), 3.52 (d, 2H), 3.29 (s, 2H), 3.15-3.10 (m, 4H), 3.00 (t, 2H)), 2.77 (t, 2H), 2.15 (d, 2H), 1.96 (d, 2H), 1.89-1.49 (m, 8H).

TEST EXAMPLE

Determination of Compounds' Inhibition of $H^+/K^+$ ATPase Enzyme Activity

The following experiment is used to determine the inhibitory effect of the compound of the present invention on the H+/K+ATPase enzyme activity.

1. Experimental Materials
Plate reader: SpectraMax M5(MD)
Malachite Green (Sigma Aldrich, 213020-25G)
Ammonium molybdate (Sigma Aldrich, 277908-20G)
ATP (Sigma Aldrich, A1852-1VL).

2. Buffer Preparation
Enzyme working solution: titrating the enzyme, diluting the enzyme with buffer 1, and during the reaction, taking 5 μl of the diluted solution into 50 μl reaction system.
ATP solution: 100 mM ATP was diluted to 5 mM with no K+buffer, and 5 μl of the diluted solution was added to the 50 μl reaction system, that is, the final concentration of ATP was 500 μM.
MLG color development liquid: 0.12% MLG, 7.5% ammonium molybdate, 11% Tween-20 was mixed as 100: 25:2, and adding 15 μl of the mixture into each well during detection.
Buffer 1: 50 mM Tris-HCl pH 6.5, 5 mM magnesium chloride (magnesium chloride), 10 μM valinomycin (valinomycin).
Buffer 2: 50 mM Tris-HCl pH 6.5, 5 mM magnesium chloride (magnesium chloride), 10 μM valinomycin (valinomycin), 20 mM KCl.
Homogenization buffer: 10 mmol/L Tris-HCl, pH 6.8, 0.25M sucrose (sucrose), 1 mmol/LEDTA
7.5% Ficoll layering solution: homogenization buffer+ 7.5% (W/W) (Ficoll 400).

3. Experimental Steps
3.1. $H^+/K^+$ ATPase Enzyme Extraction
(1) The stomach tissue of the rabbit was separated, and the blood was washed with tap water, food residue.
(2) The fundus portion was thoroughly washed with pre-cooled NaCl solution to remove surface mucus.
(3) The stripped mucosa was filled into a sample bag or a 50 ml centrifuge tube, and quickly freezing in a liquid nitrogen tank.
(4) The tissue was removed, minced with surgical scissors, and a pre-cooled homogenization buffer (4 ml/g tissue) was added and homogenized in a tissue homogenizer for 2 to 10 minutes.
(5) After homogenization, if there were larger tissue particles, they could be removed by centrifugation (600 g, 10 min), and then the supernatant was transferred to a clean centrifuge tube. After centrifugation at 20000 g for 30 minutes, then the supernatant was transferred to a clean centrifuge tube at 100000 g for 90 minutes and the precipitate was collected.
(6) Resuspending the precipitate with homogenization buffer, blowing uniformly, adding 7.5% Ficoll layering solution at equal ratio, centrifuging at 100000 g for 90 minutes, and collecting the precipitate.
(7) Resuspending the precipitate with homogenization buffer, blowing uniformly, and the protein concentration was measured by Bradford. Freezing in tubes at −80° C. for later use.

3.2. $H^+/K^+$ ATPase Activity Experiment
(1) Adding 35 μl of reaction buffer to each experimental well, and then added 35 μl of buffer 1.
(2) Adding 5 μl buffer 1 containing 10% DMSO to the whole enzyme and buffer well.
(3) Adding 5 μl of 10× compound working solution to the compound well and mixing well.
(4) Adding 5 μl of buffer 1 to the buffer well.
(5) Adding 5 μl of 10× enzyme working solution to the remaining wells, mixing and incubating at 37° C. for 30 minutes
(6) Adding 5 μl of 10× ATP working solution to all experimental wells, and incubating at 37° C. for 20 min.
(7) Adding 15 μl MLG chromogenic solution to all experimental wells, and uniformly mixing and incubating at room temperature for 5-30 min.
(8) The reading number of 620 nm was detected by an M5 instrument.

4. Data Analysis
The inhibition rate is calculated with the following formula:

Inhibition rate ($IC_{50}$)=[OD (sample well)−OD (full enzyme well containing potassium chloride)]/ [(OD (full enzyme well containing potassium chloride)−(OD (full enzyme well without potassium chloride Enzyme hole)]×100%

5. Experimental Results
The inhibition rate ($IC_{50}$) of each example compound is shown in Table 2.

TABLE 2

| Compound number | $IC_{50}$ (μM) |
| --- | --- |
| Example 1 | 0.4105 |
| Example 2 | 0.4312 |
| Example 3 | 1.861 |
| Example 4 | 0.5803 |
| Example 5 | 2.579 |

As can be seen from Table 2, the compounds of the present invention have excellent H+/K+ ATPase enzyme inhibitory activity and can be used to prepare gastric acid secretion inhibitors.

The invention claimed is:
1. A compound represented by general formula (I) or a pharmaceutically acceptable salt thereof,

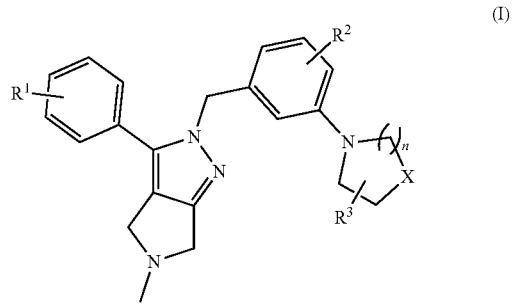

wherein:
$R^1$ is selected from hydrogen atom, chlorine, bromine, iodine or $C_{1-5}$ alkyl;
$R^2$ is selected from halogen, hydroxyl or $C_{1-5}$ alkyl;
n=1 or 2;
$R^3$ is connected to a carbon atom, X is $CH_2$, $R^3$ is selected from $NR^bR^c$, and $R^b$ and $R^c$ are linked together and form a six-membered heterocyclic ring with the N to which they are linked.

2. A pharmaceutical composition, comprising the compound or the pharmaceutically acceptable salt thereof of claim 1 and a pharmaceutically acceptable carrier, excipient or diluent.

* * * * *